(12) United States Patent
Yan et al.

(10) Patent No.: US 11,895,912 B2
(45) Date of Patent: Feb. 6, 2024

(54) ORGANIC PHOTOACTIVE LAYER COMPOSITE INK, ORGANIC SOLAR CELL AND PREPARATION METHODS THEREOF

(71) Applicant: Suzhou Institute of Nano-Tech and Nano-Bionics (Sinano), Chinese Academy of Sciences, Suzhou (CN)

(72) Inventors: Lingpeng Yan, Suzhou (CN); Jinduo Yi, Suzhou (CN); Mingxi Tan, Suzhou (CN); Changqi Ma, Suzhou (CN)

(73) Assignee: Suzhou Institute of Nano-Tech and Nano-Bionics, Chinese Academy of Sciences, Suzhou (CN)

( * ) Notice: Subject to any disclaimer, the term of this patent is extended or adjusted under 35 U.S.C. 154(b) by 670 days.

(21) Appl. No.: 16/485,700

(22) PCT Filed: Dec. 29, 2017

(86) PCT No.: PCT/CN2017/119957
§ 371 (c)(1),
(2) Date: Aug. 13, 2019

(87) PCT Pub. No.: WO2018/161707
PCT Pub. Date: Sep. 13, 2018

(65) Prior Publication Data
US 2019/0393423 A1   Dec. 26, 2019

(30) Foreign Application Priority Data
Mar. 16, 2017  (CN) .......................... 201710126348.9

(51) Int. Cl.
*H10K 85/60* (2023.01)
*C09D 11/102* (2014.01)
(Continued)

(52) U.S. Cl.
CPC ........... *H10K 85/654* (2023.02); *C09D 11/03* (2013.01); *C09D 11/102* (2013.01); *C09D 11/38* (2013.01);
(Continued)

(58) Field of Classification Search
CPC ............. H01L 51/0067; H01L 51/0007; H01L 51/0036; H01L 51/0043; H01L 51/0047;
(Continued)

(56) References Cited

U.S. PATENT DOCUMENTS

| | | | |
|---|---|---|---|
| 2009/0176995 A1* | 7/2009 | Toru ...................... | C01B 32/156 568/33 |
| 2015/0122335 A1* | 5/2015 | Yoon ................... | H01L 31/0322 136/264 |

(Continued)

FOREIGN PATENT DOCUMENTS

CN        106410037 A   *   2/2017

OTHER PUBLICATIONS

"Triethylenetetramine." National Center for Biotechnology Information. PubChem Compound Database, U.S. National Library of Medicine, https://pubchem.ncbi.nlm.nih.gov/compound/Triethylenetetramine. 2022 (Year: 2022).*

*Primary Examiner* — Kourtney R S Carlson
(74) *Attorney, Agent, or Firm* — Wang Law Firm, Inc.

(57) ABSTRACT

The disclosure discloses an organic photoactive layer composite ink, an organic solar cell and preparation methods thereof. The organic photoactive layer composite ink includes an electron donor material, an electron acceptor material, an organic amine compound and an organic solvent. According to the disclosure, through an interaction between the organic amine compound and a photoactive layer material molecule, the photochemical reaction of the active layer molecule can be effectively inhibited, the pho- (Continued)

| 1 |
|---|
| 2 |
| 3 |
| 4 |
| 5 |
| 6 | tostability of the photoactive layer material is significantly improved, and hence the stability of the solar cell is greatly improved. The organic solar cell prepared by the disclosure has the advantages of high stability, long use service life and the like, and working properties such as energy conversion efficiency are also effectively improved; meanwhile, the organic solar cell is simple and convenient in preparation process, low in material cost and high in economic benefits.

20 Claims, 6 Drawing Sheets

(51) Int. Cl.
| | |
|---|---|
| *H10K 85/10* | (2023.01) |
| *H10K 85/20* | (2023.01) |
| *H10K 30/00* | (2023.01) |
| *H10K 102/00* | (2023.01) |
| *C09D 11/03* | (2014.01) |
| *C09D 11/38* | (2014.01) |
| *C09D 11/52* | (2014.01) |
| *H10K 71/15* | (2023.01) |

(52) U.S. Cl.
CPC .............. *C09D 11/52* (2013.01); *H10K 71/15* (2023.02); *H10K 85/113* (2023.02); *H10K 85/151* (2023.02); *H10K 85/215* (2023.02); *H10K 85/60* (2023.02); *H10K 85/621* (2023.02); *H10K 85/624* (2023.02); *H10K 85/626* (2023.02); *H10K 85/655* (2023.02); *H10K 85/6572* (2023.02); *H10K 85/6576* (2023.02); *H10K 30/00* (2023.02); *H10K 2102/351* (2023.02)

(58) Field of Classification Search
CPC .............. H01L 51/005; H01L 51/0053; H01L 51/0056; H01L 51/0058; H01L 51/0068; H01L 51/0072; H01L 51/0074; H01L 51/42; H01L 2251/558; C09D 11/03; C09D 11/102; C09D 11/38; C09D 11/52
See application file for complete search history.

(56) References Cited

U.S. PATENT DOCUMENTS

2016/0087219 A1* 3/2016 Kim ............... H10K 85/631
                                                            564/429
2018/0016456 A1* 1/2018 Wang ............... C09D 11/106

\* cited by examiner

ORGANIC PHOTOACTIVE LAYER COMPOSITE INK, ORGANIC SOLAR CELL AND PREPARATION METHODS THEREOF

TECHNICAL FIELD

The disclosure particularly relates to an organic solar cell photoactive layer composite ink material, a high-stability organic solar cell formed by utilizing the organic solar cell photoactive layer composite ink material and preparation methods thereof, belonging to the technical fields of photoelectric function materials and devices.

BACKGROUND

An organic solar cell has gained more and more attention due to its low price, light weight, good bending property, large area printing and other advantages. In recent years, with unremitting efforts of scientists, the photoelectric conversion efficiency of the organic solar cell has exceeded 11% and gradually approaches a commercialization threshold. In comparison, the stability property of the current organic solar cell device is far from satisfying application demands.

Considerable research results show that during the working, the organic solar cell can generate a phenomenon of rapid attenuation, called "burn-in loss", in the beginning 100 hours. This process generally occurs in the initial working period of the device. Although it lasts for 100 hours, the properties of the device are attenuated by 20-50%, thereby seriously influencing the stability and service life of the device. Such the process is considered as attenuation of the properties of the device caused by failure in the organic photoactive layer. Thus, improvement of the stability property of the photoactive layer is an important method for improving the stability of the organic solar cell device. At present, the method for improving the stability of the photoactive layer structure is performed mainly through design synthesis of a donor material and development and use of a non-fullerene material, and there are few appropriate manners which do not affect the efficiency of the device and can improve the stability of the device on the premise that the material in the active layer is not changed.

SUMMARY

The main objective of the disclosure is to provide an organic photoactive layer composite ink and a preparation method thereof to overcome the shortages of the prior art.

Another main objective of the disclosure is to provide an organic solar cell prepared by utilizing the organic photoactive layer composite ink and a preparation method thereof.

In order to achieve the aforementioned objectives, the disclosure adopts the following technical solution:

An embodiment of the disclosure provides an organic photoactive layer composite ink, comprising an electron donor material, an electron acceptor material, an organic solvent and an organic amine compound, wherein, in the organic photoactive layer composite ink, the mass of the organic amine compound is 0.01 wt %~10 wt % of the total mass of the electron donor material and the electron acceptor material; in the organic photoactive layer composite ink, the mass ratio of the electron donor material to the electron acceptor material is 10:1~1:10, and the concentration of the electron donor material or the electron acceptor material is 1~50 mg/mL.

Further, the organic amine compound comprises an organic amine compound having a structure as shown in any one of Formulas (1), (2), (1-1) and (2-1):

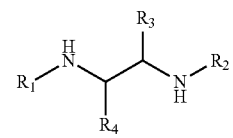

Formula (1)

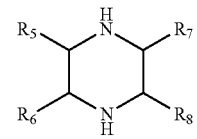

Formula (2)

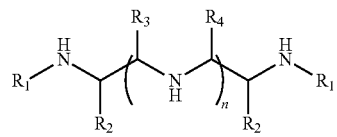

Formula (1-1)

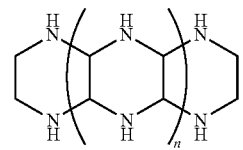

Formula (2-1)

wherein, $R_1$, $R_2$, $R_3$ and $R_4$ comprise hydrogen, substituted or unsubstituted C1~C20 alkyl, C1~C20 heteroalkyl, or substituted or unsubstituted modified aromatic or heteroaromatic π conjugated unit derivatives; $R_5$, $R_6$, $R_7$ and $R_8$ comprise hydrogen, substituted or unsubstituted C1~C20 alkyl, C1~C20 heteroalkyl, substituted or unsubstituted modified aromatic or heteroaromatic π conjugated unit derivatives, or a five or six membered cyclic structure formed by connecting any two substitution units in $R_5$, $R_6$, $R_7$ and $R_8$.

An embodiment of the disclosure also provides a preparation method of the aforementioned organic photoactive layer composite ink, comprising: dissolving an organic amine compound, an electron acceptor material and an electron donor material into an organic solvent, and uniformly mixing to obtain the organic photoactive layer composite ink.

An embodiment of the disclosure also provides an organic photoactive layer composite film formed by the aforementioned organic photoactive layer composite ink.

Further, the disclosure also provides a preparation method of the aforementioned organic photoactive layer composite film, comprising: performing film formation treatment on the organic photoactive layer composite ink to form the organic photoactive layer composite film.

Preferably, the film formation treatment manner comprises at least one of a dropping film process, a spin-coating film formation process, a spray-coating film formation process, an ink-jet printing film-formation process, a silk-screen printing film formation process, a blade coating film formation process and a wire bar coating process.

The disclosure also provides application of the aforementioned organic photoactive layer composite ink or organic photoactive layer composite film in preparation of an organic solar cell.

The disclosure also provides an organic solar cell, comprising a top electrode, a top electrode interface modification layer, an organic photoactive layer, a bottom electrode interface modification layer, a bottom electrode and a bottom electrode base which are arranged in turn along a setting direction, wherein, the organic photoactive layer comprises the aforementioned organic photoactive layer composite film. Further, the organic solar cell also comprises a bottom electrode base on which the bottom electrode is arranged.

The disclosure also provides a laminated organic solar cell whose front junction and/or rear junction cells contain the above organic solar cell.

Further, the disclosure also provides a preparation method of the aforementioned organic solar cell, comprising:

(1) providing a bottom electrode base, and arranging a bottom electrode on the bottom electrode base;

(2) forming a bottom electrode interface modification layer on the bottom electrode;

(3) forming an organic photoactive layer composite film on the bottom electrode interface modification layer by using the aforementioned organic photoactive layer composite ink;

(4) forming a top electrode interface modification layer on the organic photoactive layer composite film; and (5) forming a top electrode on the top electrode interface modification layer to obtain the organic solar cell.

Compared with the prior art, the disclosure has the advantages:

(1) for the organic photoactive layer composite ink provided by the disclosure, the organic amine compound is added in the existing photoactive layer ink, and through an interaction between the organic amine compound and the photoactive layer material molecule, the photochemical reaction of the active layer molecule is inhibited, the photostability of the photoactive layer material can be improved, and hence the stability of the solar cell is improved;

(2) through introduction of the organic amine compound, the organic photoactive layer composite ink provided by the disclosure can not only improve the photoelectric conversion efficiency of the organic solar cell but also enhance its long-term stability;

Since the organic photoactive layer composite film prepared from the organic photoactive layer composite ink provided by the disclosure is excellent in stability, the prepared organic solar cell based on this structure has high stability and long service life, and especially is capable of improving the energy conversion efficiency and other working properties of the organic solar cell device; and (4) the high-stability organic solar cell provided by the disclosure is wide in preparation method universality, and is simple and convenient in preparation method, low in material cost and high in economic benefits.

Figure 1:
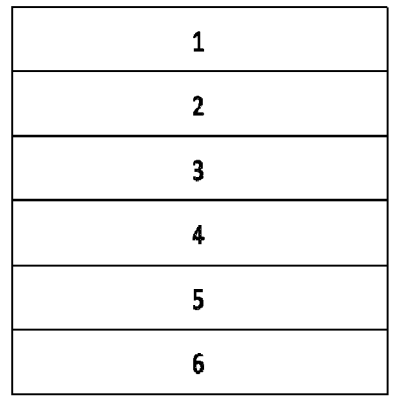
FIG. 1 is a structural diagram of an organic solar cell according to an exemplary embodiment of the disclosure.

Reference numbers: 1—top electrode, 2—top electrode interface modification layer, 3—organic photoactive layer, 4—bottom electrode interface modification layer, 5—bottom electrode, and 6—bottom electrode base.

DESCRIPTION OF THE EMBODIMENTS

In view of the shortages of the prior art, the present inventor provides the technical solution of the disclosure via long-term research and significant practice. Next, this technical solution, its implementation process and principle and the like will be further explained and illustrated.

One aspect of an embodiment of the disclosure provides an organic photoactive layer composite ink, comprising an electron donor material, an electron acceptor material, an organic solvent and an organic amine compound.

Further, in the organic photoactive layer composite ink, the mass of the organic amine compound is 0.01 wt %~10 wt % of the total mass of the electron donor material and the electron acceptor material.

Further, in the organic photoactive layer composite ink, the mass ratio of the electron donor material to the electron acceptor material is 10:1~1:10, preferably, 5:1~1:5, and more preferably, 2:1~1:2.

Further, the concentration of the electron donor material or the electron acceptor material is 1~50 mg/mL, preferably, 5~20 mg/mL, and especially preferably, 10~20 mg/mL.

The organic solvent includes, but is not limited to o-dichlorobenzene, chlorobenzene, chloroform, methylbenzene, xylene and trimethylbenzene.

Further, the organic amine compound comprises one or more organic amine compounds having a structure as shown in any one of Formulas (1), (2), (1-1) and (2-1):

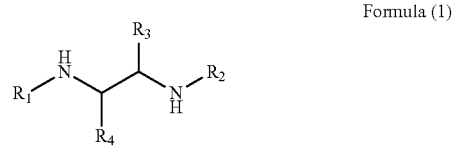

Formula (1)

Formula (2)

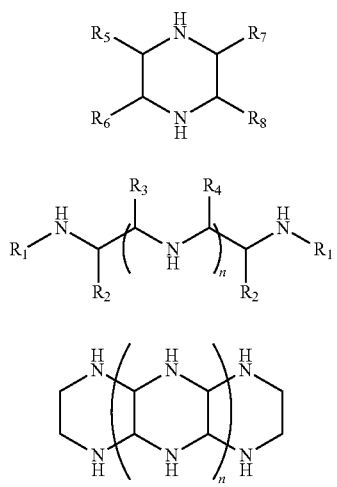

Formula (1-1)

Formula (2-1)

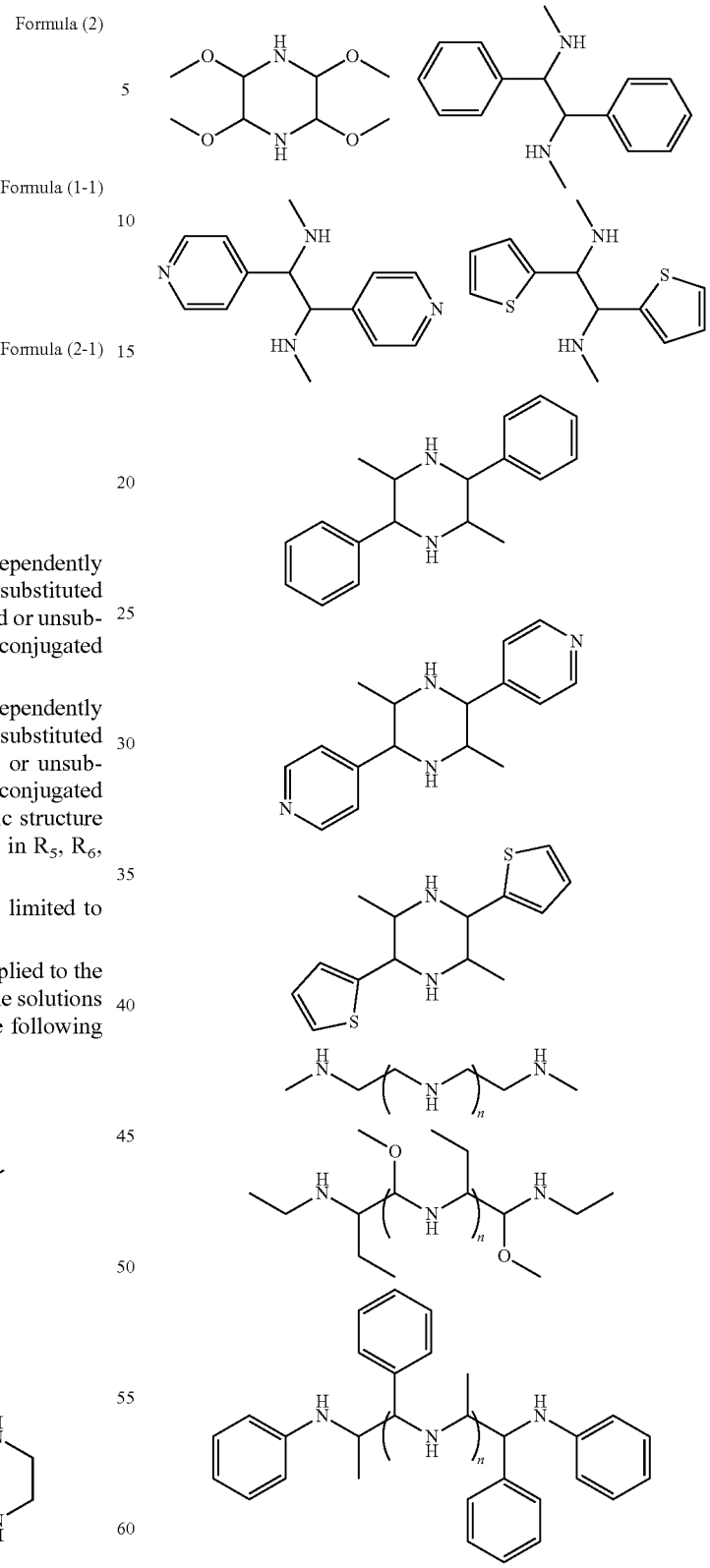

wherein, $R_1$, $R_2$, $R_3$ and $R_4$ are at least independently selected from hydrogen, substituted or unsubstituted C1~C20 alkyl, C1~C20 heteroalkyl, or substituted or unsubstituted modified aromatic or heteroaromatic π conjugated unit derivatives;

wherein, $R_5$, $R_6$, $R_7$ and $R_8$ are at least independently selected from hydrogen, substituted or unsubstituted C1~C20 alkyl, C1~C20 heteroalkyl, substituted or unsubstituted modified aromatic or heteroaromatic π conjugated unit derivatives, or a five or six membered cyclic structure formed by connecting any two substitution units in $R_5$, $R_6$, $R_7$ and $R_8$.

Preferably, C1~C20 alkyl includes, but is not limited to methyl, ethyl, propyl and butyl.

The followings are some modification units applied to the solutions disclosed by the disclosure, however, the solutions provided by the disclosure are not limited to the following units.

In some embodiments, the organic amine compound having a structure as shown in Formula (1) is selected from ethanediamine derivatives having a structure as shown in Formula (3).

Formula (3)

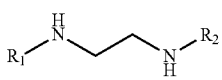

wherein, $R_1$ and $R_2$ are at least independently selected from hydrogen, substituted or unsubstituted C1~C20 alkyl, C1~C20 heteroalkyl, or substituted or unsubstituted modified aromatic or heteroaromatic π conjugated unit derivatives.

The followings are some modification units applied to the solutions disclosed by the disclosure, however, the solutions provided by the disclosure are not limited to the following units.

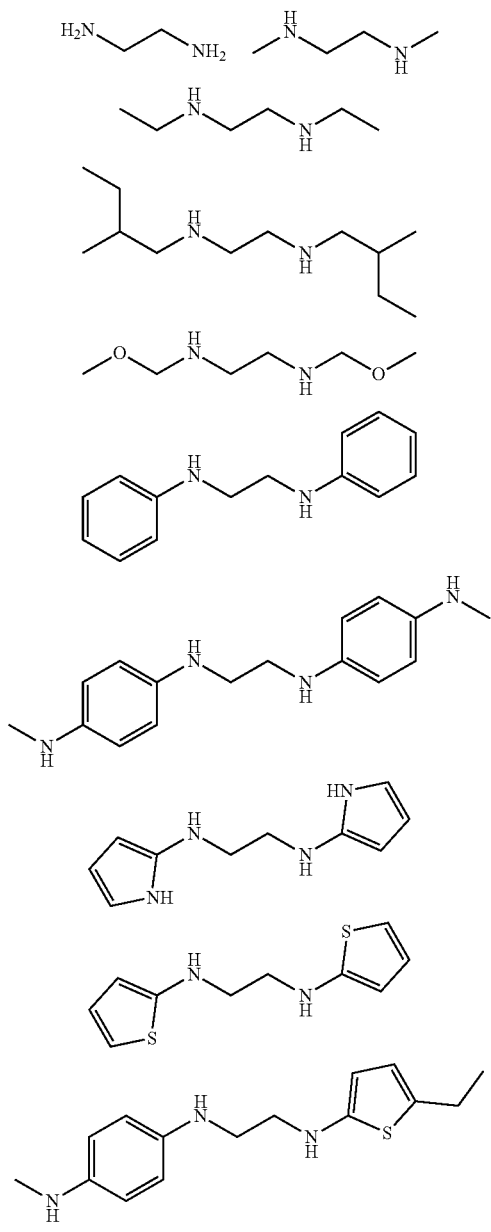

Preferably, the organic amine compound is alkyl ethanediamine.

In some embodiments, the organic amine compound having a structure as shown in Formula (2) is selected from piperazine derivatives having a structure as shown in any one of Formulas (4)-(8):

Formula (4)

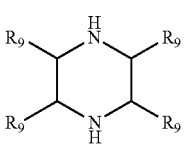

Formula (5)

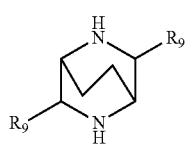

Formula (6)

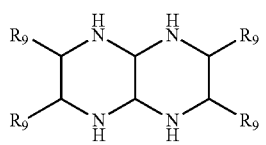

Formula (7)

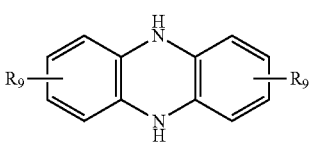

Formula (8)

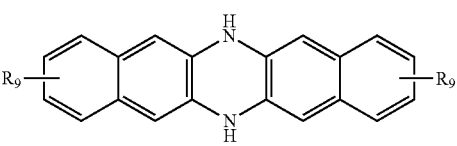

wherein, $R_9$ is at least selected from hydrogen, substituted or unsubstituted C1~C20 alkyl, C1~C20 heteroalkyl, or substituted or unsubstituted modified aromatic or heteroaromatic π conjugated unit derivatives.

The followings are some modification units applied to the solutions disclosed by the disclosure, however, the solutions provided by the disclosure are not limited to the following units.

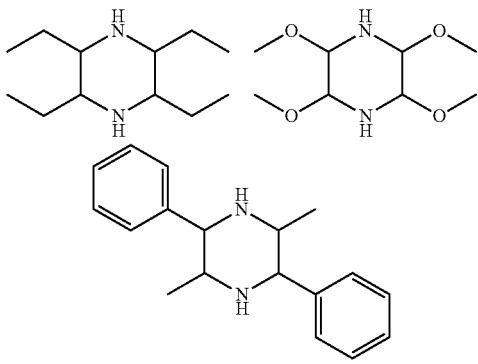

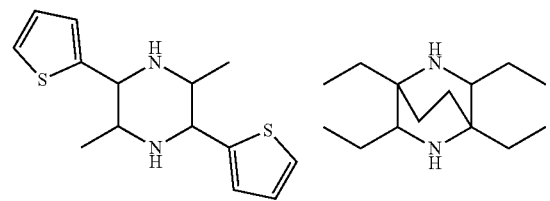
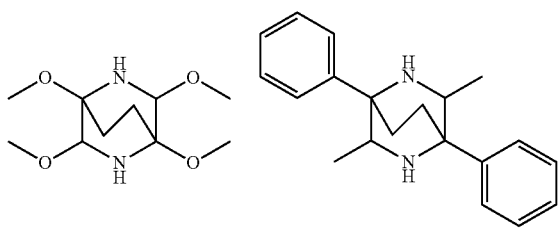
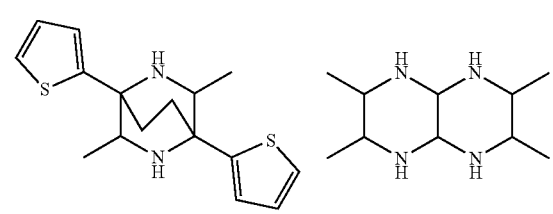
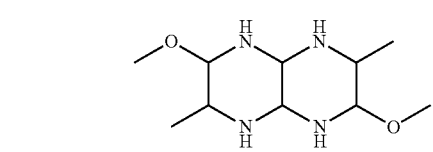
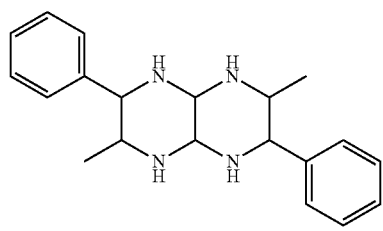
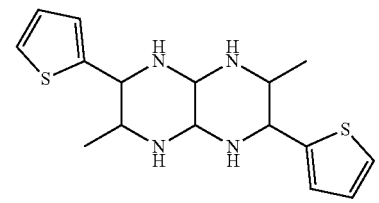
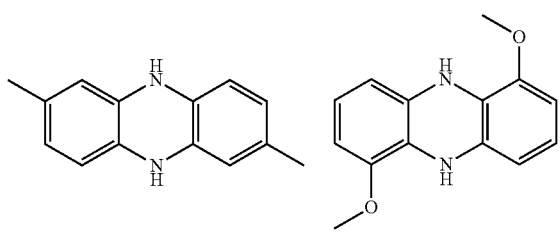
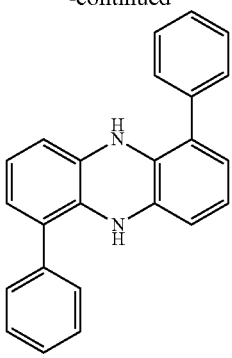
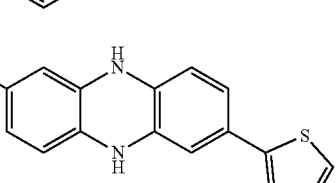
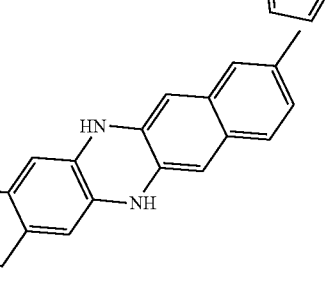
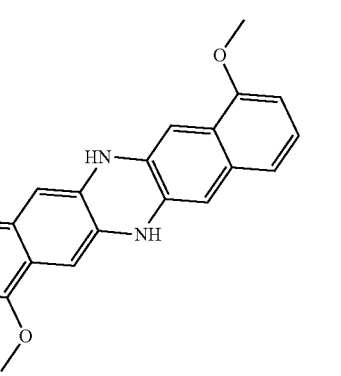
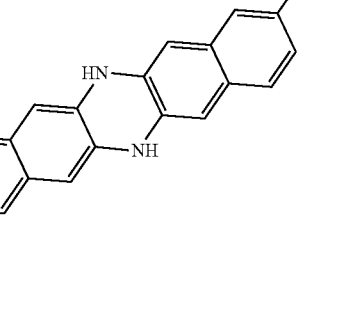
Preferably, the organic amine compound is piperazine.
The electron donor material refers to a semiconductor material whose molecule can give electrons in an organic solar cell photoactive layer under the condition of light excitation so as to achieve charge separation. In some embodiments, the electron donor material comprises a conjugated polymer electron donor material and/or a conjugated small organic molecule electron donor material.

Preferably, the conjugated polymer electron donor material comprises any one or a combination of two or more of poly(3-hexylthiophene), PTB7, PTB7-Th (Energy Environ. Sci., 2015, 8, 2902), PffBT4T-2OD (Nature communications, 2014, 5) and structure variants thereof, but is not limited thereto.

Preferably, the conjugated small organic molecule electron donor material comprises a micromolecule based on benzodithiophene (BDT) as a core and a micromolecule based on oligothiophene as a core.

For example, preferably, the conjugated small organic molecule electron donor material comprises DR3TSBDT (Advanced Materials, 2016, 28(32): 7008-7012.), DRCN7T (Nature Photonics 9.1 (2015): 35-41) and structure variants thereof.

The electron acceptor material refers to a semiconductor material whose molecule can receive electrons in an organic solar cell photoactive layer under the condition of light excitation so as to achieve charge separation. In some embodiments, the electron acceptor material comprises any one or a combination of two or more of a fullerene electron acceptor material, a fullerene derivative electron acceptor material and a non-fullerene electron acceptor material, but is not limited thereto.

Preferably, the fullerene electron acceptor material and the fullerene derivative electron acceptor material comprise any one or a combination of two or more of [6,6]-phenyl-$C_{61}$-methyl butyrate ($PC_{61}BM$), $PC_{71}BM$ (Advanced Energy Materials, 2013, 3(1): 65-74), Bis-$PC_{61}BM$ (Journal of nanoscience and nanotechnology, 2014, 14(2): 1064-1084.) and $IC_{61}BA$ (Advanced Functional Materials, 2013, 23(26): 3286-3298.), but is not limited thereto.

Preferably, the non-fullerene electron acceptor material comprises an organic conjugated electron acceptor material.

More preferably, the organic conjugated electron acceptor material comprises any one or a combination of two or more of a perylene diimide (PDI) derivative, a naphthdiimide (NDI) derivative, an indacene derivative, a fluorene derivative, a benzothiadiazole (BT) derivative and a subphthalocyanine (SubPc) derivative, but is not limited thereto.

Another aspect of an embodiment of the disclosure provides a preparation method of the aforementioned organic photoactive layer composite ink, comprising: dissolving an organic amine compound, an electron acceptor material and an electron donor material into an organic solvent, and uniformly mixing to obtain the organic photoactive layer composite ink.

Another aspect of an embodiment of the disclosure also provides an organic photoactive layer composite film formed by the aforementioned organic photoactive layer composite ink.

In some embodiments, the organic photoactive layer composite film comprises a complex formed by combination of any one or a combination of two or more of poly(3-hexylthiophene), PTB7, PTB7-Th, PffBT4T-2OD and structure variants thereof as an electron donor material, any one or a combination of two or more of [6,6]-phenyl-$C_{61}$-methyl butyrate, $PC_{71}BM$, Bis-$PC_{61}BM$ and $IC_{61}BA$ as an electron acceptor material, and an organic amine compound having a structure as shown in any one of Formulas (1), (2), (1-1) and (2-1).

Preferably, the thickness of the organic photoactive layer composite film is 80 nm~2 μm, preferably, 80~200 nm, and especially preferably, 80~100 nm.

Further, an embodiment of the disclosure also provides a preparation method of aforementioned the organic photoactive layer composite film, comprising: performing film formation treatment on the organic photoactive layer composite ink to form the organic photoactive layer composite film.

Preferably, the film formation treatment manner comprises at least one of a dropping film process, a spin-coating film formation process, a spray-coating film formation process, an ink-jet printing film formation process, a silk-screen printing film formation process, a blade coating film formation process and a wire bar coating process.

In some particular embodiments, the preparation method comprises: applying the organic photoactive layer composite ink to a substrate by at least selecting any one of coating and printing manners to construct and form the organic photoactive layer composite film.

Preferably, the coating manner comprises any one of spin coating, blade coating and spray coating.

Preferably, the film formation treatment also comprises: performing thermal treatment and/or solvent annealing treatment on the organic photoactive layer composite film.

Preferably, the organic photoactive layer composite film is subjected to thermal treatment at a temperature of 60~200° C. for 10 s~2 h.

Preferably, a solvent for the solvent annealing treatment comprises any one or a combination of two or more of methylbenzene, dimethylformamide, tetrahydrofuran, chloroform, o-dichlorobenzene and chlorobenzene, but is not limited thereto.

Further, the time for the solvent annealing treatment is 5 s~2 h.

Another aspect of an embodiment of the disclosure also provides application of the aforementioned organic photoactive layer composite ink or organic photoactive layer composite film in preparation of an organic solar cell.

Referring to FIG. 1, an embodiment of the disclosure also provides an organic solar cell, comprising a top electrode 1, a top electrode interface modification layer 2, an organic photoactive layer 3, a bottom electrode interface modification layer 4, a bottom electrode 5 and a bottom electrode base 6 which are arranged in turn along a setting direction, and the organic photoactive layer 3 comprises the aforementioned organic photoactive layer composite film.

The disclosure also provides a laminated organic solar cell whose front junction and/or rear junction cells contain the above organic solar cell.

Further, an embodiment of the disclosure also provides a preparation method of the aforementioned solar cell, comprising:

(1) providing a bottom electrode base, and arranging a bottom electrode on the bottom electrode base;

(2) forming a bottom electrode interface modification layer on the bottom electrode;

(3) forming an organic photoactive layer composite film on the bottom electrode interface modification layer by using the aforementioned organic photoactive layer composite ink;

(4) forming a top electrode interface modification layer on the organic photoactive layer composite film; and (5) forming a top electrode on the top electrode interface modification layer to obtain the organic solar cell.

Further, in the aforementioned step (1), the bottom electrode base is washed before the bottom electrode is formed on the bottom electrode base.

In some embodiments, the step (4) comprises: performing thermal treatment and/or solvent annealing treatment on the organic photoactive layer composite film, and then preparing a top electrode interface modification layer on the organic photoactive layer composite film.

Preferably, the organic photoactive layer composite film is subjected to thermal treatment at a temperature of 60~200° C. for 10 s~2 h.

Preferably, a solvent for the solvent annealing treatment comprises any one or a combination of two or more of methylbenzene, dimethylformamide (DMF), tetrahydrofuran, chloroform, o-dichlorobenzene and chlorobenzene, but is not limited thereto.

Further, the time of the solvent annealing treatment is 5 s~2 h.

Further, any step prior to the step (3) also comprises: preparing the organic photoactive layer composite ink.

In some particular embodiments, the preparation method particularly comprises the following steps:

(1) washing an indium tin oxide (ITO) base;

(2) spin coating or blade coating or spray coating a bottom electrode interface modification layer on a bottom electrode base;

(3) preparing an organic photoactive layer composite ink, then performing spin coating or blade coating or spray coating on the bottom electrode interface modification layer by using the organic photoactive layer composite ink to form an organic photoactive layer composite film;

(4) performing thermal treatment or solvent annealing treatment on the organic photoactive layer composite film, and then depositing a top electrode interface modification layer on the organic photoactive layer composite film; and (5) depositing a top electrode on the top electrode interface modification layer, thereby obtaining the organic solar cell.

In order to make the purposes, technical solutions and advantages of the disclosure more clear, the technical solutions of the disclosure will be further described in detail in combination with embodiments and drawings below. If not especially stated, the methods in the following embodiments are all conventional methods in the art.

Comparative Example 1: Preparation of an Inverted Polymer Organic Solar Cell Based on poly(3-hexylthiophene) (P3HT):[6,6]-phenyl-$C_{61}$-methyl Butyrate ($PC_{61}BM$) as an Organic Photoactive Layer First, a substrate consisting of a transparent substrate and an indium tin oxide (ITO) transparent conducting cathode sequentially undergoes ultrasonic washing with a washing agent, deionized water, acetone and isopropanol, with each step for 30 min. After being dried with nitrogen, the washed substrate is treated for 30 min using a UVO ozone washing machine. A ZnO cathode buffer layer is prepared on the treated substrate. ZnO acetone solution is spin coated on the substrate by using a spin coating method, the rotation speed of a spin coater is 2000 rpm/s, and spin coating time is 60 s. Then, annealing is carried out for 10 min at 120° C. An organic photoactive layer is prepared on the cathode buffer layer by using the spin coating method. This organic photoactive layer is prepared by dissolving an electron donor material P3HT and an electron acceptor material $PC_{61}BM$ into o-dichlorobenzene in a mass percent of 1:1 to be mixed. The organic photoactive layer is prepared in a glove box by using the spin coating method, with the rotation speed of 600 rpm/s, time of 60 s and a thickness of about 150 nm. After spin-coating film formation, solvent annealing is carried out for 2 h in a watch glass with a cover, and then the substrate is put on a heating plate and undergoes thermal annealing for 30 min at 120° C. Subsequently, the substrate is brought into a vacuum coating machine, anode buffer layer molybdenum oxide ($MoO_3$) (a thickness is 20 nm, and an evaporation rate is 0.5-1 Å/s) and metal anode Al (a thickness is 100 nm, and an evaporation rate is 8 Å/s) are sequentially deposited on the organic photoactive layer. The prepared solar cell is measured under standard conditions (AM1.5, 100 mW/cm$^2$), and current density-voltage curve data is collected using a Keithley 2400 digital source table.

The structure of the organic solar cell prepared in this comparative example is as follows: transparent substrate/ITO/ZnO/P3HT:$PC_{61}BM$/$MoO_3$/Al (100 nm).

Figure 2:
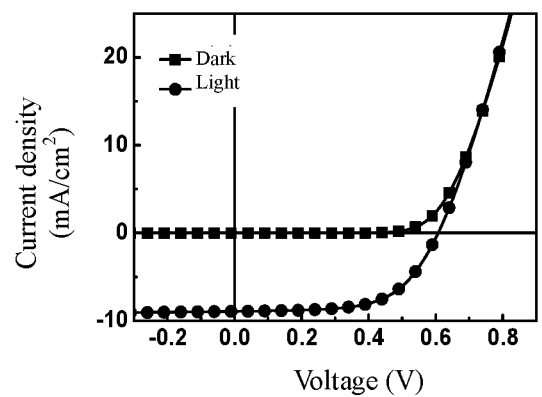
FIG. 2 is an I-V curve graph of an organic solar cell prepared according to a comparative example 1 of the disclosure.

Referring to FIG. 2, it is a current density-voltage curve graph of an organic solar cell prepared in comparative example 1, and other specific device property parameters are listed in Table 1. It can be seen from experimental results that the photoelectric conversion efficiency of a P3HT:$PC_{61}BM$ cell having a standard structure is 3.30%.

TABLE 1

| Property Parameters Of P3HT:$PC_{61}$BM Device | | | | |
|---|---|---|---|---|
| | $V_{OC}$ (V) | $J_{SC}$ (mA/cm$^2$) | FF | PCE (%) |
| P3HT:$PC_{61}$BM | 0.61 | 9.02 | 0.60 | 3.30 |

Embodiment 1: Preparation of an Inverted Polymer Organic Solar Cell Based on poly(3-hexylthiophene) (P3HT): [6,6]-phenyl-$C_{61}$-methyl Butyrate ($PC_{61}BM$):Piperazine (Different Contents) as an Organic Photoactive Layer A preparation method is seen in comparative example 1. This organic photoactive layer is prepared by dissolving an electron donor material P3HT, an electron acceptor material $PC_{61}BM$ and piperazine into o-dichlorobenzene to be mixed, wherein, the mass percent of P3HT to $PC_{61}BM$ is 1:1, and the contents of piperazine are respectively 1 wt %, 3 wt %, 5 wt %, 7 wt % and 10 wt % of the total masses of P3HT and $PC_{61}BM$. The structure of the organic solar cell prepared in this embodiment is as follows: transparent substrate/ITO/ZnO/P3HT:$PC_{61}BM$:piperazine/Al (100 nm), wherein, the structure of piperazine is seen in Formula (9).

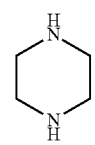

Formula (9)

TABLE 2

| Property Parameters Of P3HT:$PC_{61}$BM Device Having Different Piperazine Contents | | | | |
|---|---|---|---|---|
| Addition amounts of piperazine | $V_{OC}$ (V) | $J_{SC}$ (mA/cm$^2$) | FF | PCE (%) |
| 1% | 0.62 | 10.11 | 0.59 | 3.70 |
| 3% | 0.62 | 9.61 | 0.60 | 3.57 |
| 5% | 0.62 | 9.53 | 0.59 | 3.49 |

TABLE 2-continued

Property Parameters Of P3HT:PC$_{61}$BM Device Having Different Piperazine Contents

| Addition amounts of piperazine | V$_{OC}$ (V) | J$_{SC}$ (mA/cm$^2$) | FF | PCE (%) |
|---|---|---|---|---|
| 7% | 0.61 | 9.89 | 0.56 | 3.38 |
| 10% | 0.61 | 9.59 | 0.56 | 3.28 |

Figure 3:
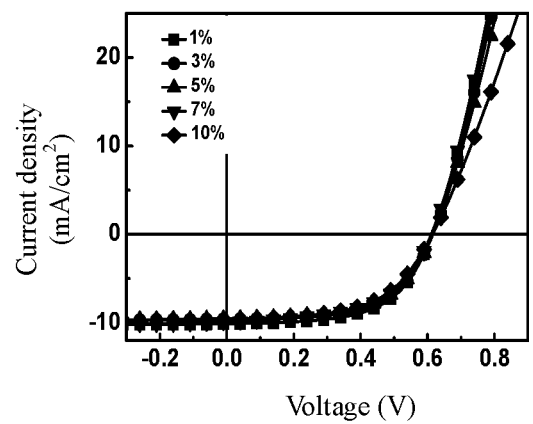
FIG. 3 is an I-V curve graph of an organic solar cell prepared according to embodiment 1 of the disclosure.

Referring to FIG. 3, it is a current density-voltage curve graph of an organic solar cell prepared in embodiment 1, and other specific device property parameters are listed in Table 2. It can be seen from experimental results that when the doping amount of piperazine is 1-5%, the voltage and current of the organic solar cell are both increased, and the photoelectric conversion efficiency of the final device is 3.70% to the greatest extent. When the doping amount ranges from 1% to 10%, the properties of the device are all higher than or equal to those of the device without doping of piperazine, illustrating the doping range of piperazine is extremely wide.

Embodiment 2: Preparation of an Inverted Polymer Organic Solar Cell Based on poly(3-hexylthiophene) (P3HT): [6,6]-phenyl-C$_{61}$-methyl Butyrate (PC$_{61}$BM):N,N'-dimethyl Ethylenediamine (1 wt %) as an Organic Photoactive Layer A preparation method is seen in comparative example 1. This organic photoactive layer is prepared by dissolving an electron donor material P3HT, an electron acceptor material PC$_{61}$BM and N,N'-dimethyl ethylenediamine into o-dichlorobenzene to be mixed, wherein, the mass percent of P3HT to PC$_{61}$BM is 1:1, and the content of N,N'-dimethyl ethylenediamine is 1 wt % of the total mass of P3HT and PC$_{61}$BM. The structure of the organic solar cell prepared in this embodiment is as follows: transparent substrate/ITO/ZnO/P3HT:PC$_{61}$BM:N,N'-dimethyl ethylenediamine/MoO$_3$/Al (100 nm), wherein, the structure of N,N'-dimethyl ethylenediamine is seen in Formula (10).

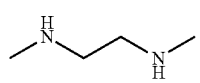

Formula (10)

TABLE 3

Property Parameters Of P3HT:PC$_{61}$BM Device containing 1 wt % of N,N'-dimethyl ethylenediamine

| | V$_{OC}$ (V) | J$_{SC}$ (mA/cm$^2$) | FF | PCE (%) |
|---|---|---|---|---|
| N,N'-dimethyl ethylenediamine (1%) | 0.62 | 9.55 | 0.59 | 3.49 |

Figure 4:
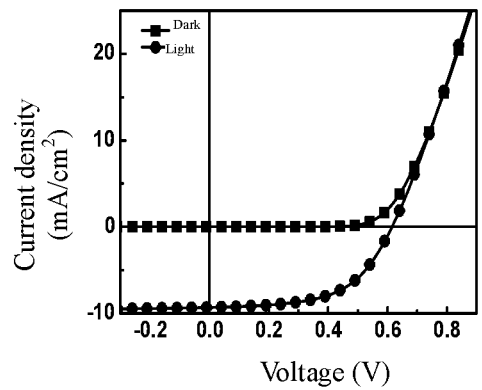
FIG. 4 is an I-V curve graph of an organic solar cell prepared according to embodiment 2 of the disclosure.

Referring to FIG. 4, it is a current density-voltage curve graph of an organic solar cell prepared in embodiment 2, and other specific device property parameters are listed in Table 3. It can be seen from experimental results that after 1 wt % of N,N'-dimethyl ethylenediamine is doped, the voltage and current of the organic solar cell are both increased, and the photoelectric conversion efficiency of the final device is improved from original 3.30% to 3.49%.

Embodiment 3: Preparation of an Inverted Polymer Organic Solar Cell Based on poly(3-hexylthiophene) (P3HT): [6,6]-phenyl-C$_{61}$-methyl Butyrate (PC$_{61}$BM):Decahydroisoquinoline (1 wt %) as an Organic Photoactive Layer A preparation method is seen in comparative example 1. This organic photoactive layer is prepared by dissolving an electron donor material P3HT, an electron acceptor material PC$_{61}$BM and decahydroisoquinoline into o-dichlorobenzene to be mixed, wherein, the mass percent of P3HT to PC$_{61}$BM is 1:1, and the content of decahydroisoquinoline is 1 wt % of the total mass of P3HT and PC$_{61}$BM. The structure of the organic solar cell prepared in this embodiment is as follows: transparent substrate/ITO/ZnO/P3HT:PC$_{61}$BM:decahydroisoquinoline/MoO$_3$/Al (100 nm), wherein, the structure of decahydroisoquinoline is seen in Formula (11).

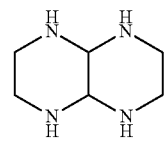

Formula (11)

TABLE 4

Property Parameters Of P3HT:PC$_{61}$BM Device containing 1 wt % of decahydroisoquinoline

| | V$_{OC}$ (V) | J$_{SC}$ (mA/cm$^2$) | FF | PCE (%) |
|---|---|---|---|---|
| Decahydroisoquinoline (1%) | 0.62 | 9.77 | 0.58 | 3.51 |

Figure 5:
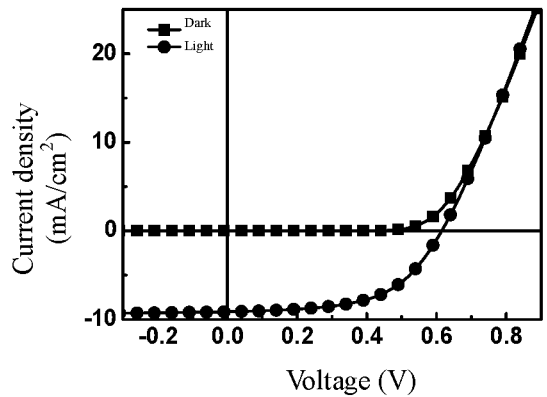
FIG. 5 is an I-V curve graph of an organic solar cell prepared according to embodiment 3 of the disclosure.

Referring to FIG. 5, it is a current density-voltage curve graph of an organic solar cell prepared in embodiment 3, and other specific device property parameters are listed in Table 4. It can be seen from experimental results that after 1 wt % of decahydroisoquinoline is doped, the voltage and current of the organic solar cell are both increased, and the photoelectric conversion efficiency of the final device is improved from original 3.30% to 3.51%.

Embodiment 4: Preparation of an Inverted Polymer Organic Solar Cell Based on PTB7-Th: [6,6]-phenyl-C$_{61}$-methyl Butyrate (PC$_{61}$BM):Piperazine (Different Concentrations) as an Organic Photoactive Layer A preparation method is seen in comparative example 1. This organic photoactive layer is prepared by dissolving an electron donor material PTB7-Th, an electron acceptor material PC$_{61}$BM and piperazine (different concentrations) into chlorobenzene (added with DIO having a volume ratio of 3%) to be mixed, wherein, the mass percent of PTB7-Th to PC$_{61}$BM is 1:1.2, the concentration of PTB7-Th is 7 mg/mL, and the content of piperazine is 0.01-0.2 wt % of the total mass of PTB7-Th and PC$_{61}$BM. The organic photoactive layer is prepared in a glove box by using a spin coating method, with a rotation speed of 1000 rpm/s, time of 60 s and a thickness of about 100 nm. The structure of the organic solar cell prepared in this embodiment is as follows: transparent substrate/ITO/ZnO/P3HT:PTB7-Th:PC$_{61}$BM:piperazine/MoO$_3$/Al (100 nm), wherein, the chemical structure of PTB7-Th is seen in Formula (12).

Formula (12)

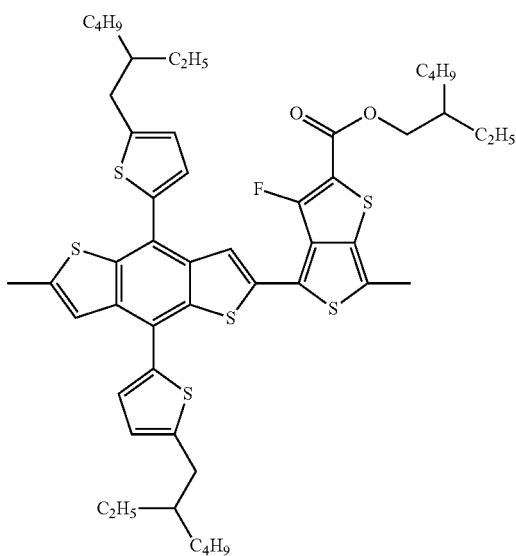

TABLE 5

Property Parameters Of PTB7-Th:PC$_{61}$BM Device containing different piperazine contents

| Addition amount of piperazine | $V_{OC}$ (V) | $J_{SC}$ (mA/cm$^2$) | FF | PCE (%) |
|---|---|---|---|---|
| 0.01% | 0.8 | 14.42 | 0.50 | 5.77 |
| 0.05% | 0.8 | 14.73 | 0.41 | 4.83 |
| 0.1% | 0.8 | 14.61 | 0.51 | 5.96 |
| 0.15% | 0.8 | 14.67 | 0.64 | 7.51 |
| 0.2% | 0.8 | 14.88 | 0.57 | 6.79 |

Figure 6:
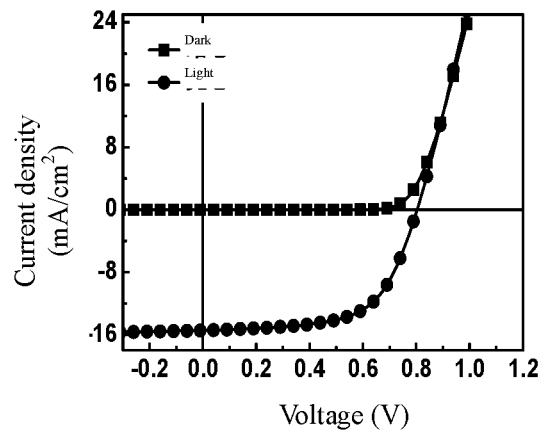
FIG. 6 is an I-V curve graph of an organic solar cell prepared according to embodiment 4 of the disclosure.

Referring to FIG. 6, it is a current density-voltage curve graph of a 0.15 wt % piperazine-doped organic solar cell prepared in embodiment 4. It can be seen from experimental results that after 0.15 wt % of piperazine is doped, the photoelectric conversion efficiency of the organic solar cell is 7.51%.

Embodiment 5: Preparation of a Forward Polymer Solar Cell Based on COOP-4HT-BDT (Micromolecule):PC$_{71}$BM:Piperazine (0.1 wt %) as an Organic Photoactive Layer First, a substrate consisting of a transparent substrate and an indium tin oxide (ITO) transparent conducting cathode sequentially undergoes ultrasonic washing with a washing agent, deionized water, acetone and isopropanol, with each step for 30 min. After being dried with nitrogen, the washed substrate is treated for 30 min using a UVO ozone washing machine. A PEDOT:PSS anode buffer layer is prepared on the treated substrate. The organic photoactive layer is prepared on the anode buffer layer by using a spin coating method. This organic photoactive layer is prepared by dissolving an electron donor material COOP-4HT-BDT, an electron acceptor material PC$_{71}$BM and piperazine into chloroform to be mixed, wherein, in the mass percent of COOP-4HT-BDT to PC$_{71}$BM is 2:1, the concentration of COOP-4HT-BDT is 5 mg/mL, and the content of piperazine is 0.1 wt % of the total mass of COOP-4HT-BDT and PC$_{71}$BM. An organic photoactive layer is prepared in a glove box by using the spin coating method, with the rotation speed of 2500 rpm/s, time of 40 s and a thickness of about 110 nm. Then, the substrate is brought into a vacuum coating machine, and cathode buffer layer lithium fluoride (LiF) (a thickness is 1 nm, and an evaporation rate is 2 Å/s) and metal cathode Al (a thickness is 100 nm, and an evaporation rate is 8 Å/s) are sequentially deposited on the organic photoactive layer. The prepared organic solar cell is measured under standard conditions (AM1.5, 100 mW/cm$^2$), and current density-voltage curve data is collected using a Keithley 2400 digital source table.

The structure of the organic solar cell prepared in this embodiment is as follows: transparent substrate/ITO/PEDOT:PSS/COOP-4HT-BDT:PC$_{71}$BM:piperazine/LiF/Al (100 nm), wherein, the structure of COOP-4HT-BDT is seen in Formula (13).

Formula (13)

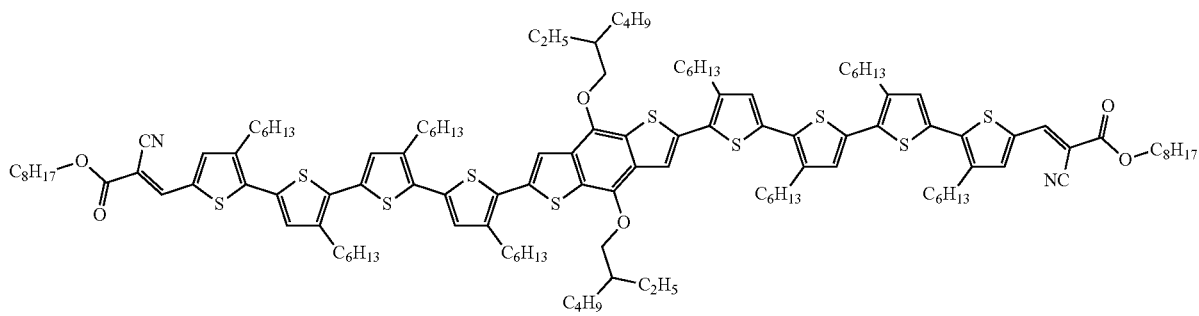

TABLE 6

Property Parameters Of COOP-4HT-BDT:PC$_{71}$BM Containing 0.1 wt % Of Piperazine

| | $V_{OC}$ (V) | $J_{SC}$ (mA/cm$^2$) | FF | PCE (%) |
|---|---|---|---|---|
| COOP-4HT-BDT:PC$_{71}$BM:piperazine | 0.90 | 8.27 | 0.69 | 5.14 |

Figure 7:
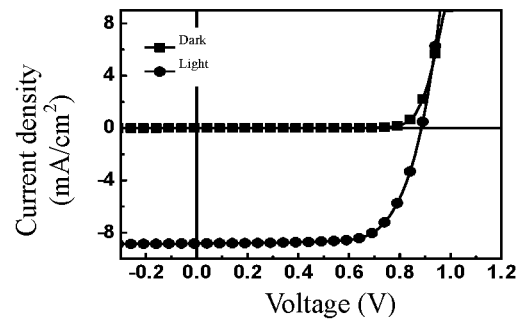
FIG. 7 is an I-V curve graph of an organic solar cell prepared according to embodiment 5 of the disclosure.

Referring to FIG. 7, it is a current density-voltage curve graph of an organic solar cell prepared in embodiment 5, and other specific device property parameters are listed in Table 6. It can be seen from experimental results that after 1 wt % of piperazine is doped, the photoelectric conversion efficiency of the organic solar cell is 5.14%.

Embodiment 6: Preparation of an Inverted Polymer Organic Solar Cell Based on PTB7-Th:SBF-PDI$_4$:Piperazine (0.1 wt %) as an Organic Photoactive Layer A preparation method is seen in comparative example 1. This organic photoactive layer is prepared by dissolving an electron donor material PTB7-Th, an electron acceptor material SBF-PDI$_4$ and piperazine into chloroform (added with chloronaphthalene having a volume ratio of 1%) to be mixed, wherein, the mass percent of PTB7-Th to SBF-PDI$_4$ is 1:1, the concentration of PTB7-Th is 5 mg/mL, the content of piperazine is 0.1 wt % of the total mass of PTB7-Th and SBF-PDI$_4$. The organic photoactive layer is prepared in a glove box by using a spin coating method, with a rotation speed of 2000 rpm/s, time of 60 s and a thickness of about 100 nm. The structure of the organic solar cell prepared in this embodiment is as follows: transparent substrate/ITO/ZnO/PTB7-Th:SBF-PDI$_4$:piperazine/MoO$_3$/Al (100 nm), wherein, the structure of PTB7-Th is seen in Formula (14).

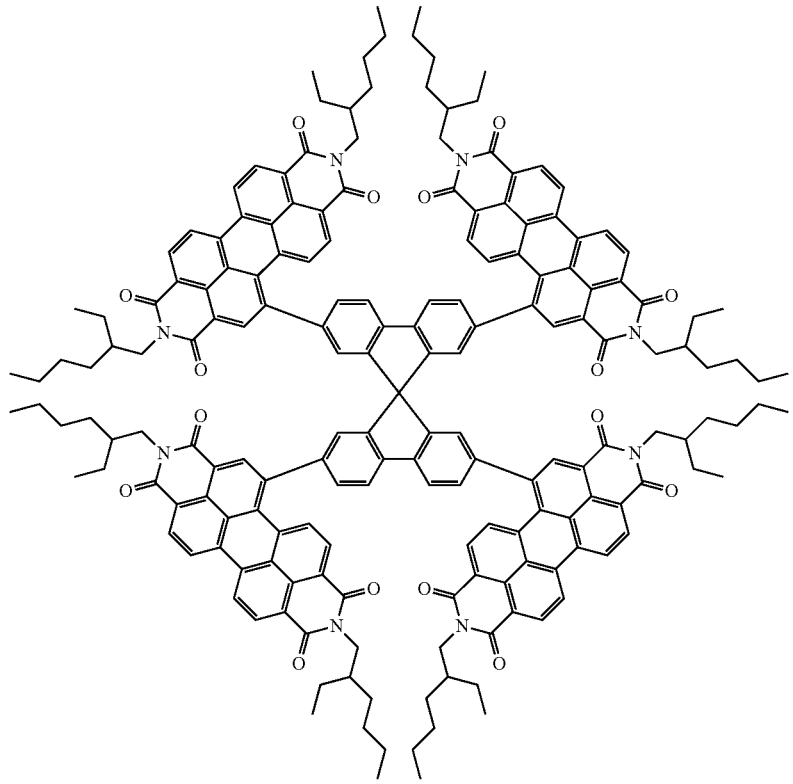

Formula (14)

TABLE 7

Property Parameters Of PTB7-Th:SBF-PDI$_4$ Device

| | $V_{OC}$ (V) | $J_{SC}$ (mA/cm$^2$) | FF | PCE (%) |
|---|---|---|---|---|
| PTB7-Th:SBF-PDI$_4$:piperazine | 0.85 | 13.05 | 0.48 | 5.32 |

Figure 8:
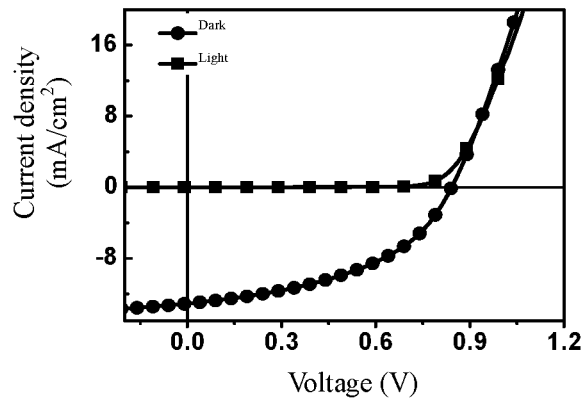
FIG. 8 is an I-V curve graph of an organic solar cell prepared according to embodiment 6 of the disclosure.

As shown in FIG. 8, it is a current density-voltage curve graph of an organic solar cell prepared in embodiment 6, and other specific device properties are listed in Table 7. It can be seen from experimental results that after 0.1 wt % of piperazine is doped, the photoelectric conversion efficiency of the organic solar cell is 5.32%.

Embodiment 7: Preparation of an Inverted Polymer Organic Solar Cell Based on P3HT:PC$_{61}$BM:Polyetherimide (1 wt %) as an Organic Photoactive Layer A preparation method is seen in comparative example 1. This organic photoactive layer is prepared by dissolving an electron donor material P3HT, an electron acceptor material PC$_{61}$BM and polyetherimide into o-dichlorobenzene to be mixed, wherein, the mass percent of P3HT to PC$_{61}$BM is 1:1, the content of polyetherimide is 1 wt % of the total mass of P3HT and PC$_{61}$BM. The structure of the organic solar cell prepared in this embodiment is as follows: transparent substrate/ITO/ZnO/P3HT:PC$_{61}$BM:polyetherimide/MoO$_3$/Al (100 nm), wherein, the structure of polyetherimide is seen in Formula (15).

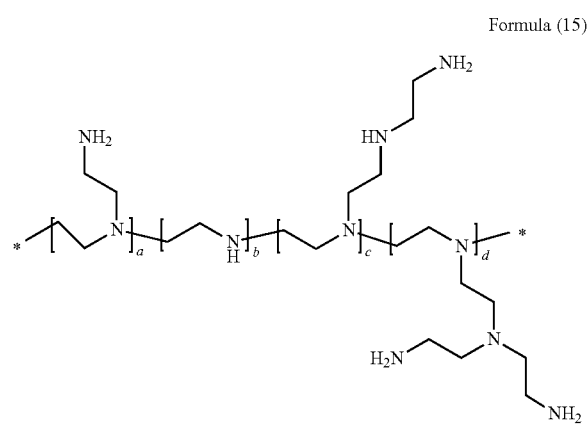

Formula (15)

TABLE 8

Property Parameters Of P3HT:PC$_{61}$BM Device Containing 1 wt % Of Polyetherimide

|  | $V_{OC}$ (V) | $J_{SC}$ (mA/cm$^2$) | FF | PCE (%) |
| --- | --- | --- | --- | --- |
| Polyetherimide (1%) | 0.61 | 9.53 | 0.62 | 3.60 |

Figure 9:
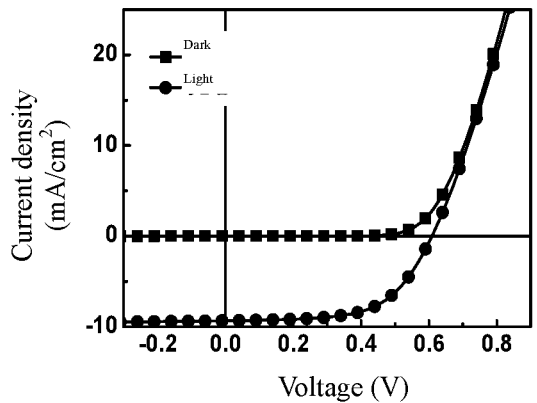
FIG. 9 is an I-V curve graph of an organic solar cell prepared according to embodiment 7 of the disclosure.

Referring to FIG. 9, it is a current density-voltage curve graph of an organic solar cell prepared in embodiment 7, and other specific device properties are listed in Table 8. It can be seen from experimental results that after 1 wt % of polyetherimide is doped, the voltage and current of the organic solar cell are both increased, and the photoelectric conversion efficiency of the final device is improved from original 3.30% to 3.60%.

Embodiment 8: Preparation of an Inverted Polymer Organic Solar Cell Based on P3HT:PC$_{61}$BM:2,5-diazabicyclo [2.2.2] octane (1 wt %) as an Organic Photoactive Layer A preparation method is seen in comparative example 1. This organic photoactive layer is prepared by dissolving an electron donor material P3HT, an electron acceptor material PC$_{61}$BM and 2,5-diazabicyclo [2.2.2] octane into o-dichlorobenzene to be mixed, wherein, the mass percent of P3HT to PC$_{61}$BM is 1:1, and the content of 2,5-diazabicyclo [2.2.2] octane is 1 wt % of the total mass of P3HT and PC$_{61}$BM. The structure of the organic solar cell prepared in this embodiment is as follows: transparent substrate/ITO/ZnO/P3HT:PC$_{61}$BM:2,5-diazabicyclo [2.2.2] octane/MoO$_3$/Al (100 nm), wherein, the structure of 2,5-diazabicyclo [2.2.2] octane is seen in Formula (16).

Formula (16)

TABLE 9

Property Parameters Of P3HT:PC$_{61}$BM Device Containing 1 wt % Of 2,5-diazabicyclo [2.2.2] Octane

|  | $V_{OC}$ (V) | $J_{SC}$ (mA/cm$^2$) | FF | PCE (%) |
| --- | --- | --- | --- | --- |
| 2,5-diazabicyclo [2.2.2] octane (1%) | 0.61 | 9.56 | 0.63 | 3.67 |

Figure 10:
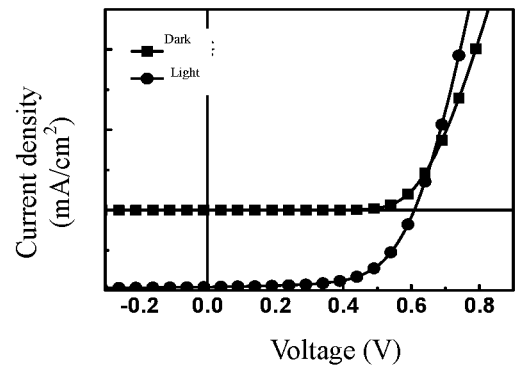
FIG. 10 is an I-V curve graph of an organic solar cell prepared according to embodiment 8 of the disclosure.

Referring to FIG. 10, it is a current density-voltage curve graph of an organic solar cell prepared in embodiment 8, and other specific device properties are listed in Table 9. It can be seen from experimental results that after 1 wt % of 2,5-diazabicyclo [2.2.2] octane is doped, the voltage and current of the organic solar cell are both increased, and the photoelectric conversion efficiency of the final device is improved from original 3.30% to 3.67%.

Embodiment 9: Preparation of an Inverted Polymer Organic Solar Cell Based on P3HT:PC$_{61}$BM:N,N'-diphenylethanediamine (1 wt %) as an Organic Photoactive Layer A preparation method is seen in comparative example 1. This organic photoactive layer is prepared by dissolving an electron donor material P3HT, an electron acceptor material PC$_{61}$BM and N,N'-diphenylethanediamine into o-dichlorobenzene to be mixed, wherein, the mass percent of P3HT to PC$_{61}$BM is 1:1, the content of N,N'-diphenylethanediamine is 1 wt % of the total mass of P3HT and PC$_{61}$BM. The structure of the organic solar cell prepared in this embodiment is as follows: transparent substrate/ITO/ZnO/P3HT:PC$_{61}$BM:N,N'-diphenylethanediamine/MoO$_3$/Al (100 nm), wherein, the structure of N,N'-diphenylethanediamine is seen in Formula (17).

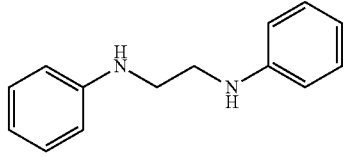

Formula (17)

TABLE 10

Property Parameters Of P3HT:PC$_{61}$BM Device Containing 1 wt % Of N,N'-diphenylethanediamine

|  | $V_{OC}$ (V) | $J_{SC}$ (mA/cm$^2$) | FF | PCE (%) |
| --- | --- | --- | --- | --- |
| N,N'-diphenylethanediamine (1%) | 0.61 | 9.48 | 0.63 | 3.64 |

Figure 11:
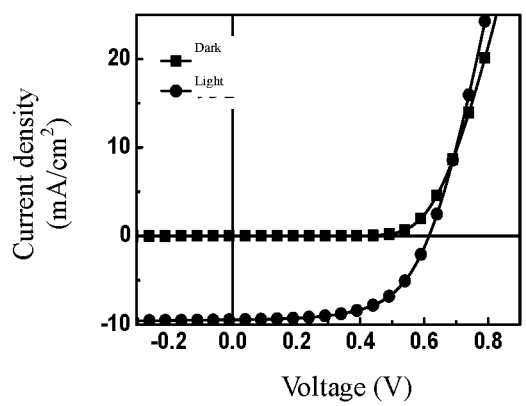
FIG. 11 is an I-V curve graph of an organic solar cell prepared according to embodiment 9 of the disclosure.

Referring to FIG. 11, it is a current density-voltage curve graph of an organic solar cell prepared in embodiment 9, and other specific device properties are listed in Table 10. It can be seen from experimental results that after 1 wt % of N,N'-diphenylethanediamine is doped, the voltage and current of the organic solar cell are both increased, and the photoelectric conversion efficiency of the final device is improved from original 3.30% to 3.64%.

Embodiment 10: Preparation of an Inverted Polymer Organic Solar Cell Based on P3HT:PC$_{61}$BM:2,5-Dimethylpiperazine (1 wt %) as an Organic Photoactive Layer A preparation method is seen in comparative example 1. This organic photoactive layer is prepared by dissolving an electron donor material P3HT, an electron acceptor material PC$_{61}$BM and 2,5-dimethylpiperazine into o-dichlorobenzene to be mixed, wherein, the mass percent of P3HT to PC$_{61}$BM is 1:1, the content of 2,5-dimethylpiperazine is 1 wt % of the total mass of P3HT and PC$_{61}$BM. The structure of the organic solar cell prepared in this embodiment is as follows: transparent substrate/ITO/ZnO/P3HT:PC$_{61}$BM:2,5-dimethylpiperazine/MoO$_3$/Al (100 nm), wherein, the structure of 2,5-dimethylpiperazine is seen in Formula (18).

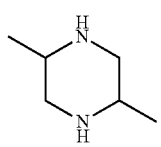

Formula (18)

TABLE 11

Property Parameters Of P3HT:PC$_{61}$BM Device Containing 1 wt % Of 2,5-dimethylpiperazine

| | $V_{OC}$ (V) | $J_{SC}$ (mA/cm$^2$) | FF | PCE (%) |
|---|---|---|---|---|
| 2,5-dimethylpiperazine (1%) | 0.61 | 9.50 | 0.62 | 3.59 |

Figure 12:
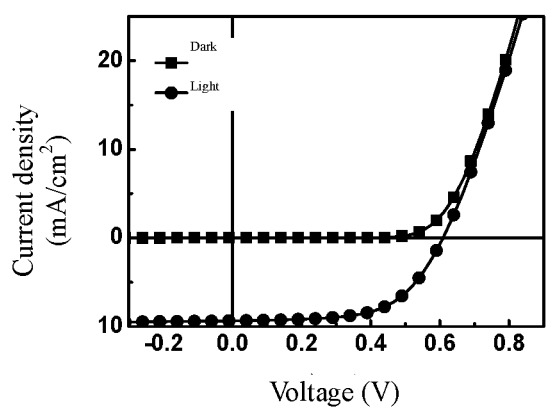
FIG. 12 is an I-V curve graph of an organic solar cell prepared according to embodiment 10 of the disclosure.

Referring to FIG. 12, it is a current density-voltage curve graph of an organic solar cell prepared in embodiment 10, and other specific device properties are listed in Table 11. It can be seen from experimental results that after 1 wt % of 2,5-dimethylpiperazine is doped, the voltage and current of the organic solar cell are both increased, and the photoelectric conversion efficiency of the final device is improved from original 3.30% to 3.59%.

Embodiment 11: Preparation of an Inverted Polymer Organic Solar Cell Based on P3HT:PC$_{61}$BM:2-(4-pyridyl)piperazine (1 wt %) as an Organic Photoactive Layer A preparation method is seen in comparative example 1. This organic photoactive layer is prepared by dissolving an electron donor material P3HT, an electron acceptor material PC$_{61}$BM and 2-(4-pyridyl) piperazine into trimethylbenzene to be mixed, wherein, the mass percent of P3HT to PC$_{61}$BM is 1:1, the content of 2-(4-pyridyl) piperazine is 1 wt % of the total mass of P3HT and PC$_{61}$BM. The structure of the organic solar cell prepared in this embodiment is as follows: transparent substrate/ITO/ZnO/P3HT:PC$_{61}$BM:2-(4-pyridyl) piperazine/MoO$_3$/Al (100 nm), wherein, the structure of 2-(4-pyridyl) piperazine is seen in Formula (19).

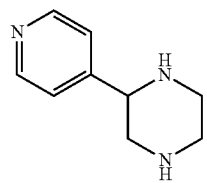

Formula (19)

TABLE 12

Property Parameters Of P3HT:PC$_{61}$BM Device Containing 1 wt % Of 2-(4-pyridyl) piperazine

| | $V_{OC}$ (V) | $J_{SC}$ (mA/cm$^2$) | FF | PCE (%) |
|---|---|---|---|---|
| 2-(4-pyridyl) piperazine (1%) | 0.61 | 9.37 | 0.62 | 3.54 |

Figure 13:
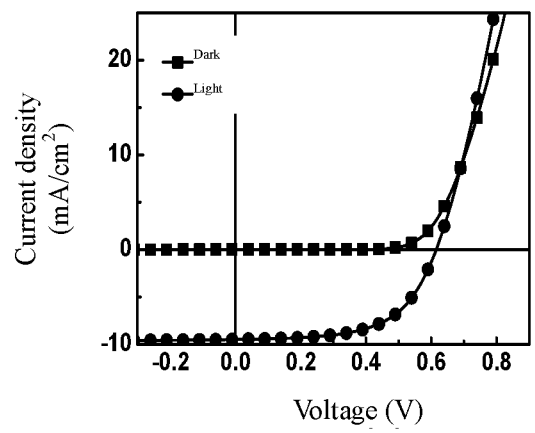
FIG. 13 is an I-V curve graph of an organic solar cell prepared according to embodiment 11 of the disclosure.

Referring to FIG. 13, it is a current density-voltage curve graph of an organic solar cell prepared in embodiment 11, and other specific device properties are listed in Table 12. It can be seen from experimental results that after 1 wt % of 2-(4-pyridyl) piperazine is doped, the voltage and current of the organic solar cell are both increased, and the photoelectric conversion efficiency of the final device is improved from original 3.30% to 3.54%.

Embodiment 12: Preparation of an Inverted Polymer Organic Solar Cell Based on P3HT:PC$_{61}$BM:Pentaethylene Hexaamine (1 wt %) as an Organic Photoactive Layer A preparation method is seen in comparative example 1. This organic photoactive layer is prepared by dissolving an electron donor material P3HT, an electron acceptor material PC$_{61}$BM and pentaethylene hexaamine into o-dichlorobenzene to be mixed, wherein, the mass percent of P3HT to PC$_{61}$BM is 1:1, and the content of pentaethylene hexaamine is 1 wt % of the total mass of P3HT and PC$_{61}$BM. The structure of the organic solar cell prepared in this embodiment is as follows: transparent substrate/ITO/ZnO/P3HT:PC$_{61}$BM:pentaethylene hexaamine/MoO$_3$/Al (100 nm), wherein, the structure of pentaethylene hexaamine is seen in Formula (20).

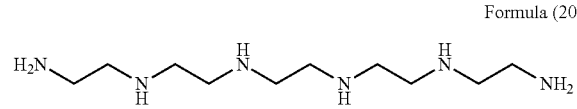

Formula (20)

TABLE 13

Property Parameters Of P3HT:PC$_{61}$BM Device Containing 1 wt % Of pentaethylene hexaamine

| | $V_{OC}$ (V) | $J_{SC}$ (mA/cm$^2$) | FF | PCE (%) |
|---|---|---|---|---|
| Pentaethylene hexaamine (1%) | 0.61 | 9.49 | 0.62 | 3.59 |

Figure 14:
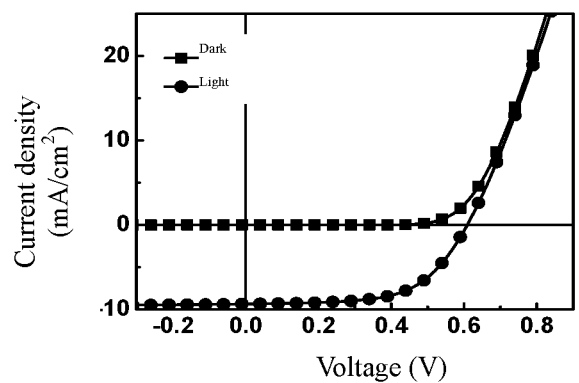
FIG. 14 is an I-V curve graph of an organic solar cell prepared according to embodiment 12 of the disclosure.

Referring to FIG. 14, it is a current density-voltage curve graph of an organic solar cell prepared in embodiment 12, and other specific device properties are listed in Table 13. It can be seen from experimental results that after 1 wt % of pentaethylene hexaamine is doped, the voltage and current of the organic solar cell are both increased, and the photoelectric conversion efficiency of the final device is improved from original 3.30% to 3.59%.

Embodiment 13: Preparation of an Inverted Polymer Organic Solar Cell Based on PffBT4T-2OD:PC$_{61}$BM:N,N'-diphenylethanediamine (1 wt %) as an Organic Photoactive Layer A preparation method is seen in comparative example 1. This organic photoactive layer is prepared by dissolving an electron donor material PffBT4T-2OD, an electron acceptor material PC$_{61}$BM and N,N'-diphenylethanediamine (Formula 20) into trimethylbenzene and 1-phenyl naphthalene to be mixed, wherein, the mass percent of PffBT4T-2OD to PC$_{61}$BM is 1:1, the content of N,N'-diphenylethanediamine is 1 wt % of the total mass of PffBT4T-2OD and PC$_{61}$BM. The volume ratio of 1-phenyl naphthalene to trimethylbenzene is 0.025:1. The structure of the organic solar cell prepared in this embodiment is as follows: transparent substrate/ITO/ZnO/PffBT4T-2OD:PC$_{61}$BM:N,N'-diphenylethanediamine/MoO$_3$/Al (100 nm), wherein, the structure of PffBT4T-2OD is seen in Formula (21) and the structure of N,N'-diphenylethanediamine is seen in Formula (17).

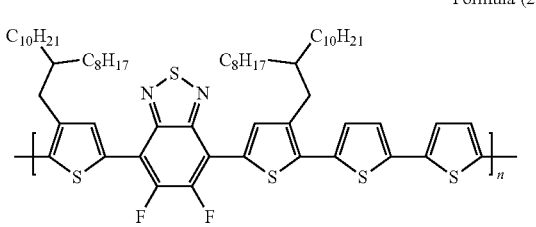

Formula (21)

TABLE 14

Property Parameters Of PffBT4T-2OD:PC$_{61}$BM Device Containing 1 wt % Of N,N'-diphenylethanediamine

| | V$_{OC}$ (V) | J$_{SC}$ (mA/cm$^2$) | FF | PCE (%) |
|---|---|---|---|---|
| N,N'-diphenylethanediamine (1%) | 0.79 | 17.50 | 0.65 | 8.92 |

Figure 15:
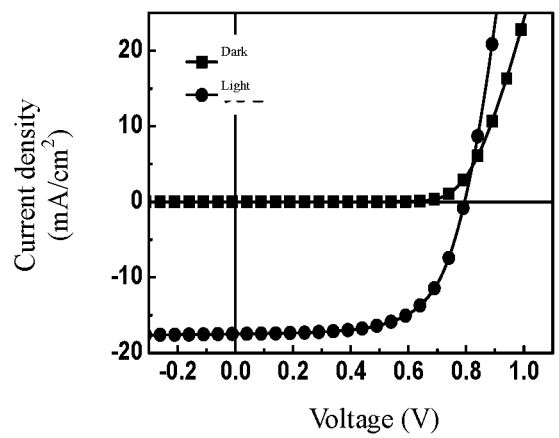
FIG. 15 is an I-V curve graph of an organic solar cell prepared according to embodiment 13 of the disclosure.

Referring to FIG. 15, it is a current density-voltage curve graph of an organic solar cell prepared in embodiment 13, and other specific device properties are listed in Table 14. It can be seen from experimental results that after 1 wt % of N,N'-diphenylethanediamine is doped, the photoelectric conversion efficiency of the device is 8.92%.

Embodiment 14: Preparation of an Inverted Polymer Organic Solar Cell Based on P3HT:PC$_{61}$BM:5,10-dihydro-phenazine (1 wt %) as an Organic Photoactive Layer A preparation method is seen in comparative example 1. This organic photoactive layer is prepared by dissolving an electron donor material P3HT, an electron acceptor material PC$_{61}$BM and 5,10-DIHYDRO-PHENAZINE into o-dichlorobenzene to be mixed, wherein, the mass percent of P3HT to PC$_{61}$BM is 1:1, the content of 5,10-DIHYDRO-PHENAZINE is 1 wt % of the total mass of P3HT and PC$_{61}$BM. The structure of the organic solar cell prepared in this embodiment is as follows: transparent substrate/ITO/ZnO/P3HT:PC$_{61}$BM: 5,10-DIHYDRO-PHENAZINE/MoO$_3$/Al (100 nm), wherein, the structure of 5,10-DI-HYDRO-PHENAZINE is seen in Formula (22).

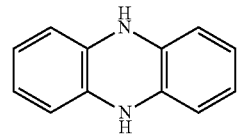

Formula (22)

TABLE 15

Property Parameters Of P3HT:PC$_{61}$BM Device Containing 1 wt % Of 5,10-DIHYDRO-PHENAZINE

| | V$_{OC}$ (V) | J$_{SC}$ (mA/cm$^2$) | FF | PCE (%) |
|---|---|---|---|---|
| 5,10-DIHYDRO-PHENAZINE (1%) | 0.61 | 9.32 | 0.63 | 3.58 |

Figure 16:
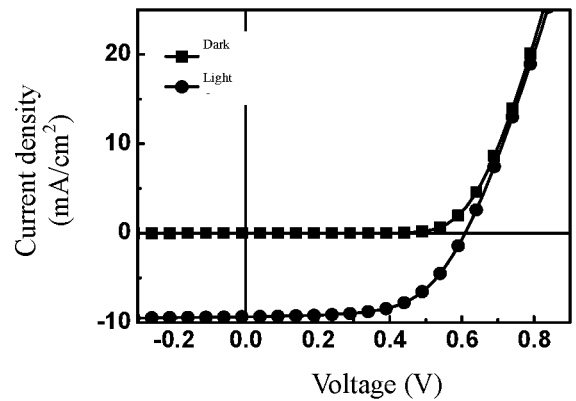
FIG. 16 is an I-V curve graph of an organic solar cell prepared according to embodiment 14 of the disclosure.

Referring to FIG. 16, it is a current density-voltage curve graph of an organic solar cell prepared in embodiment 14, and other specific device properties are listed in Table 15. It can be seen from experimental results that after 1 wt % of 5,10-DIHYDRO-PHENAZINE is doped, the voltage and current of the organic solar cell are both increased, and the photoelectric conversion efficiency of the final device is improved from original 3.30% to 3.58%.

Embodiment 15 the inverted P3HT:PC$_{61}$BM device in comparative example 1 and the 1% piperazine-doped P3HT:PC$_{61}$BM device in embodiment 1 are simultaneously subjected to an attenuation test using a solar cell service life test system. During the test, the light intensities of the two devices are consistent, and the two devices are both tested under the condition of additional 100% load. Since the devices are persistently illuminated, the temperatures of the surfaces of the devices during the test are 40-45° C.

Figure 17A:
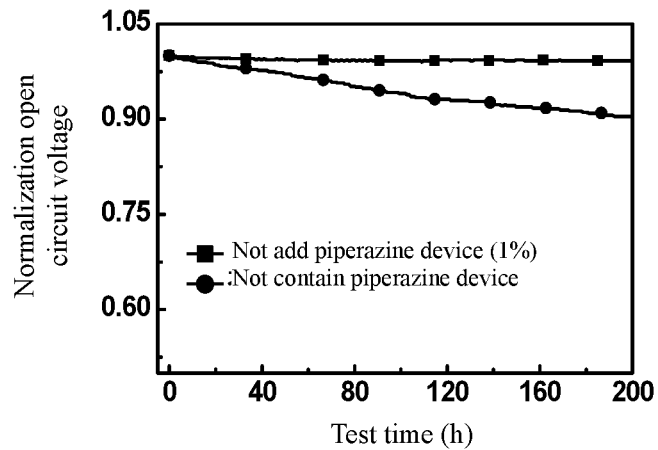
FIG. 17a-FIG. 17b are curve graphs of changes in properties of organic solar cells prepared according to comparative example 1 and embodiment 1 of the disclosure in an attenuation test over time.
Figure 17B:
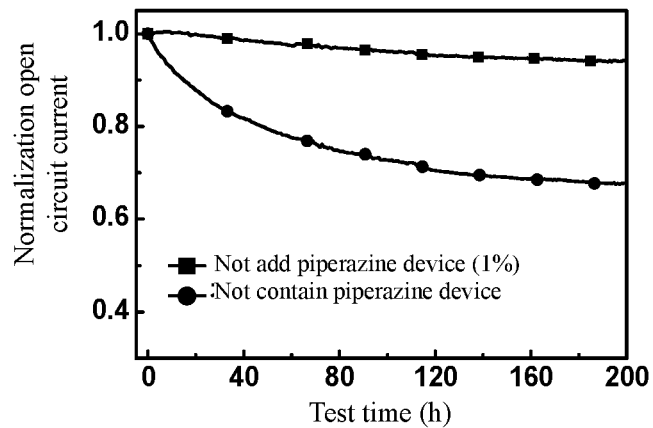

FIG. 17a-FIG. 17b are curve graphs of changes in properties of the inverted P3HT:PC$_{61}$BM device in comparative example 1 and the 1% piperazine-doped P3HT:PC$_{61}$BM device in embodiment 1 during attenuation over time. It can be seen from FIG. 17a-FIG. 17b that various parameters of the device without doping of piperazine are attenuated along with the extension of time, leading to rapid attenuation of the properties during this. When the test proceeds to 200 h, the properties of the device have been attenuated to initial 55%. However, the voltage and current of the piperazine-doped device are barely attenuated along with the extension of time, and a filling factor rises, finally leading to slight rising of the properties of the device. When the test proceeds to 200 h, the properties of the device are still barely attenuated.

Results from embodiments 1-15 illustrate that doping of organic amine compounds (such as ethanediamine and piperazine) can not only improve the efficiency of the organic solar cell but also greatly enhance the long-term stability of the device.

It should be understood that the above embodiments are only for describing the technical conception and features of the disclosure for the purpose that persons familiar with this technique can know the contents of the disclosure and accordingly implement the disclosure, and thereby cannot limit the protection scope of the disclosure. All equivalent changes or modifications made according to the spirit of the disclosure should fall within the extent of protection of the disclosure.

What is claimed is:

1. An organic photoactive layer composite ink, comprising
an electron donor material,
an electron acceptor material,
an organic solvent, and
an organic amine compound,
wherein the mass ratio of the electron donor material to the electron acceptor material is 5:1 to 1:5,
wherein the concentration of the electron donor material or the electron acceptor material is 5 to 20 mg/mL,
wherein the organic amine compound comprises an organic amine compound having a structure as shown in any one of Formulas (1), (2), (1-1), (2-1), and (4)-(8):

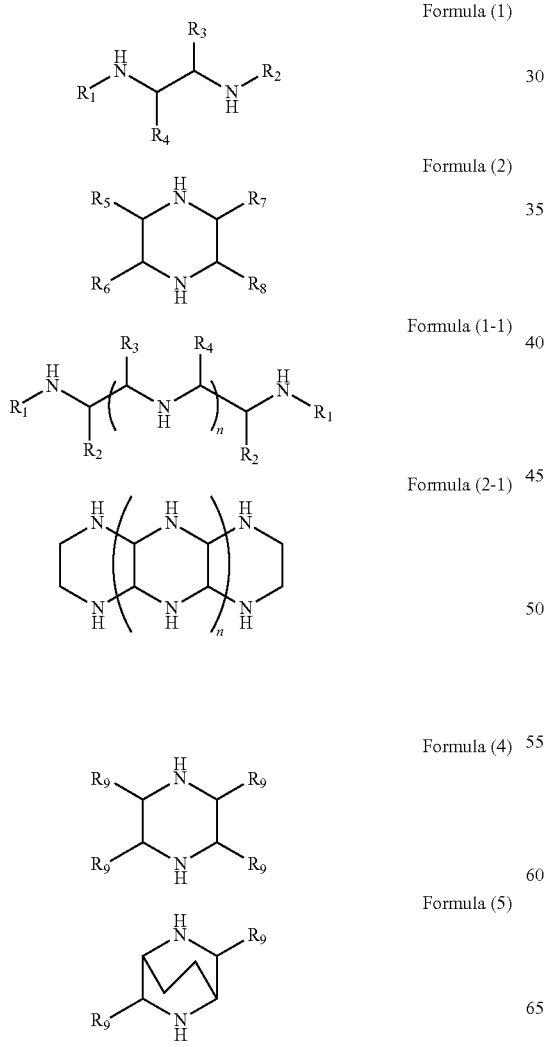

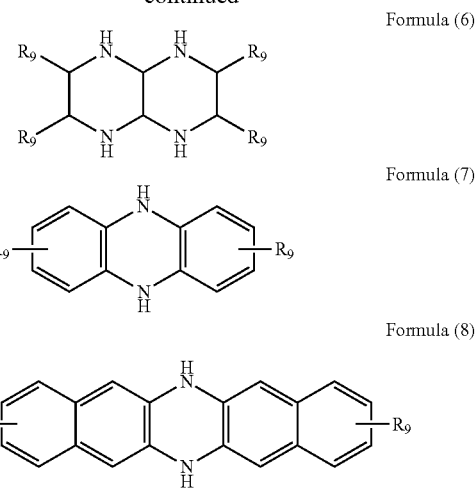

wherein, $R_1$, $R_2$, $R_3$, $R_4$, and $R_9$ comprise hydrogen, substituted or unsubstituted C1 to C20 alkyl, C1 to C20 heteroalkyl, or substituted or unsubstituted modified aromatic or heteroaromatic π conjugated unit derivatives; $R_5$, $R_6$, $R_7$ and $R_8$ comprise hydrogen, substituted or unsubstituted C1 to C20 alkyl, C1 to C20 heteroalkyl, substituted or unsubstituted modified aromatic or heteroaromatic π conjugated unit derivatives, or a five or six membered cyclic structure formed by connecting any two substitution units in $R_5$, $R_6$, $R_7$ and $R_8$,
wherein the electron donor material comprises any one or a combination of two or more of poly(3-hexylthiophene), PTB7, PTB7-Th, PffBT4T-2OD, COOP-4HT-BDT, and structure variants thereof,
wherein the electron acceptor material comprises any one or a combination of two or more of a fullerene electron acceptor material, a fullerene derivative electron acceptor material and a non-fullerene electron acceptor material, and
wherein the mass of the organic amine compound is 0.01 wt % to 0.2 wt % of the total mass of the electron acceptor material and the electron donor material that comprises any one or a combination of two or more of PTB7, PTB7-Th, COOP-4HT-BDT, and structure variants thereof, or the mass of the organic amine compound is 1 wt % to 5 wt % of the total mass of the electron acceptor material and the electron donor material that comprises any one or a combination of two or more of poly(3-hexylthiophene), PffBT4T-2OD, and structure variants thereof.

2. The organic photoactive layer composite ink according to claim 1, wherein the mass ratio of the electron donor material to the electron acceptor material is 2:1 to 1:2.

3. The organic photoactive layer composite ink according to claim 1, wherein the concentration of the electron donor material or the electron acceptor material is 10 to 20 mg/mL.

4. The organic photoactive layer composite ink according to claim 1, wherein the organic solvent comprises any one or a combination of two or more of o-dichlorobenzene, chlorobenzene, chloroform, methylbenzene, xylene and trimethylbenzene.

5. The organic photoactive layer composite ink according to claim 1, wherein the organic amine compound is selected from ethanediamine derivatives which have a structure as shown in Formula (3):

Formula (3)

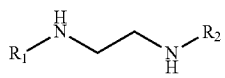

wherein, $R_1$ and $R_2$ comprise hydrogen, substituted or unsubstituted C1 to C20 alkyl, C1 to C20 heteroalkyl, or substituted or unsubstituted modified aromatic or heteroaromatic π conjugated unit derivatives.

6. The organic photoactive layer composite ink according to claim 1, wherein the organic amine compound is piperazine.

7. The organic photoactive layer composite ink according to claim 1, wherein the fullerene electron acceptor material and the fullerene derivative electron acceptor material comprise any one or a combination of two or more of [6,6]-phenyl-$C_{61}$-methyl butyrate, $PC_{71}BM$ Bis-$PC_{61}BM$ and $IC_{61}BA$, and the non-fullerene electron acceptor material comprises an organic conjugated electron acceptor material, and the organic conjugated electron acceptor material comprises any one or a combination of two or more of a perylene diimide derivative, a naphthdiimide derivative, an indacene derivative, a fluorene derivative, a benzothiadiazole derivative and a subphthalocyanine derivative.

8. A preparation method of the organic photoactive layer composite ink according to claim 1, comprising: dissolving the organic amine compound, the electron acceptor material and the electron donor material into the organic solvent, and uniformly mixing to obtain the organic photoactive layer composite ink.

9. An organic photoactive layer composite film formed by the organic photoactive layer composite ink according to claim 1, wherein the thickness of the organic photoactive layer composite film is 80 nm to 2 μm.

10. The organic photoactive layer composite film according to claim 9, comprising a complex formed by combining any one or a combination of two or more of poly(3-hexylthiophene), PTB7, PTB7-Th, PffBT4T-2OD and structure variants thereof as an electron donor material, any one or a combination of two or more of [6,6]-phenyl-$C_{61}$-methyl butyrate, $PC_{71}BM$, Bis-$PC_{61}BM$ and $IC_{61}BA$ as an electron acceptor material, and an organic amine compound having a structure as shown in any one of Formulas (1), (2), (1-1) and (2-1)

Formula (1)

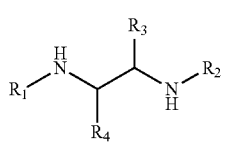

Formula (2)

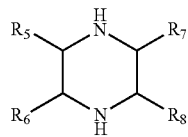

Formula (1-1)

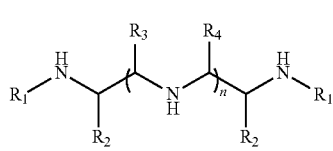

Formula (2-1)

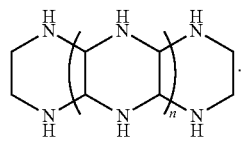

11. The organic photoactive layer composite film according to claim 9, wherein the thickness of the organic photoactive layer composite film is 80 to 100 nm.

12. A preparation method of the organic photoactive layer composite film according to claim 9, comprising: performing film formation treatment on the organic photoactive layer composite ink to form the organic photoactive layer composite film.

13. The preparation method according to claim 12, wherein, the film formation treatment manner comprises at least one of a dropping film process, a spin-coating film formation process, a spray-coating film formation process, an ink-jet printing film formation process, a silk-screen printing film formation process, a blade coating film formation process and a wire bar coating process.

14. The preparation method according to claim 12, wherein, the film formation treatment also comprises performing thermal treatment and/or solvent annealing treatment on the organic photoactive layer composite film, wherein, the organic photoactive layer composite film is subjected to thermal treatment at a temperature of 60 to 200° C. for 10 s to 2 h, and a solvent for the solvent annealing treatment comprises any one or a combination of two or more of methylbenzene, dimethylformamide, tetrahydrofuran, chloroform, o-dichlorobenzene and chlorobenzene, and the time for solvent annealing treatment is 5 s to 2 h.

15. An organic solar cell, comprising a top electrode, a top electrode interface modification layer, an organic photoactive layer, a bottom electrode interface modification layer and a bottom electrode which are arranged in turn along a setting direction, wherein, the organic photoactive layer comprises the organic photoactive layer composite film according to claim 9.

16. The organic solar cell according to claim 15, also comprising a bottom electrode base on which the bottom electrode is arranged.

17. A preparation method of the organic solar cell according to claim 15, comprising:
(1) providing a bottom electrode base, and arranging the bottom electrode on the bottom electrode base;
(2) forming the bottom electrode interface modification layer on the bottom electrode;
(3) forming the organic photoactive layer composite film on the bottom electrode interface modification layer by using the organic photoactive layer composite ink;
(4) forming the top electrode interface modification layer on the organic photoactive layer composite film; and
(5) forming the top electrode on the top electrode interface modification layer to obtain the organic solar cell.

18. The preparation method according to claim 17, wherein, the step (4) comprises: performing thermal treatment and/or solvent annealing treatment on the organic photoactive layer composite film, and then forming the top electrode interface modification layer on the organic photoactive layer composite film, wherein, a solvent for the solvent annealing treatment comprises any one or a combination of two or more of methylbenzene, dimethylformamide, tetrahydrofuran, chloroform, o-dichlorobenzene and chlorobenzene, and the time for solvent annealing treatment is 5 s to 2 h, or the organic photoactive layer composite film is subjected to thermal treatment at a temperature of 60 to 2000 C. for 10 s to 2 h.

19. The organic photoactive layer composite ink according to claim 1, wherein the mass of the organic amine compound is 1 wt % of the total mass of the electron acceptor material and the electron donor material that comprises poly(3-hexylthiophene).

20. The organic photoactive layer composite ink according to claim 1, wherein the organic amine compound is ethanediamine.

* * * * *